United States Patent [19]
Hine et al.

[11] Patent Number: 6,070,104
[45] Date of Patent: May 30, 2000

[54] MEDICAL ELECTRICAL RIGHT ATRIUM AND CORONARY SINUS LEAD

[75] Inventors: Douglas Hine, White Bear Lake, Minn.; Nicolaas Lokhoff, Kerkrade, Netherlands; Paulus Van Venrooij, Hoensbroek, Netherlands; Arnoldus Bakels, Simpelveld, Netherlands

[73] Assignee: Medtronic, Inc., Minneapolis, Minn.

[21] Appl. No.: 08/980,438

[22] Filed: Nov. 28, 1997

[51] Int. Cl.$^7$ ........................................... A61N 1/05
[52] U.S. Cl. ................................. 607/123; 607/125
[58] Field of Search ..................... 607/122–128; 600/373–375, 381

[56] References Cited

U.S. PATENT DOCUMENTS

| | | | |
|---|---|---|---|
| 3,866,613 | 2/1975 | Kenny et al. | 128/408 |
| 4,432,377 | 2/1984 | Dickhudt | 607/122 |
| 4,928,688 | 5/1990 | Mower | 128/419 PG |
| 5,265,601 | 11/1993 | Mehra | 607/9 |
| 5,304,139 | 4/1994 | Adams et al. | 607/122 |
| 5,324,327 | 6/1994 | Cohen | 607/122 |
| 5,423,772 | 6/1995 | Lurie et al. | 604/282 |
| 5,476,498 | 12/1995 | Ayers | 607/122 |
| 5,531,781 | 7/1996 | Alferness et al. | 607/122 |
| 5,545,204 | 8/1996 | Cammilli et al. | 607/123 |

FOREIGN PATENT DOCUMENTS

WO 96/15665   5/1996   WIPO .

OTHER PUBLICATIONS

NASPE Abstracts—Pacing and Clinical Electrophysiology, Apr. 1995, vol. 18, No. 4, Part II "Experience with a New Coronary Sinus Lead Specifically Designed for Permanent Left Atrial Pacing"—C. Daubert et al.

*Primary Examiner*—Jeffrey R. Jastrzab
*Attorney, Agent, or Firm*—Thomas F. Woods; Harold Patton; Michael J. Jaro

[57] ABSTRACT

A transvenous lead specifically designed for multi-chamber electrical stimulation or sensing. In a first embodiment the lead features one or more electrodes for communication with the right atrium as well as one or more electrodes for communication with either or both of the left chambers of the heart. The lead further features structures to simultaneously bring the first electrode into contact with a first chamber, such as the right atrial wall and the second electrode into contact with a particular portion of the coronary sinus wall, to electrically access the left atrium or ventricle. In the preferred embodiment the lead body has varying flex or stiffness characteristics along its length between each of the electrodes. The relation of the varying flex or stiffness characteristics along the lead body length as well as the various linear placements of the electrodes along the lead body length function to simultaneously bring the first electrode into contact with a first desired portion of the heart, such as the right atrial wall, and the second electrode into contact with a second desired portion of the heart, such as a portion of the coronary sinus wall.

20 Claims, 6 Drawing Sheets

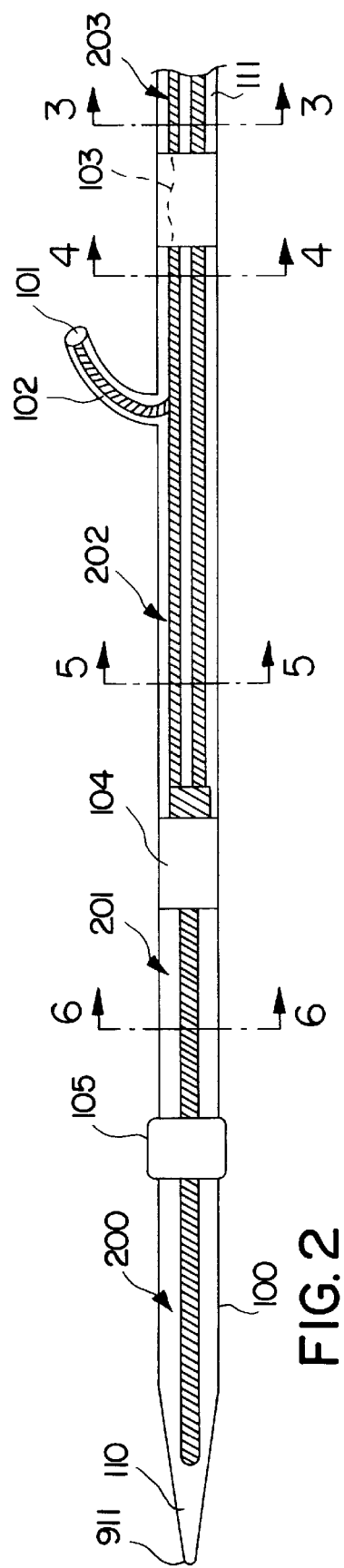
FIG. 2
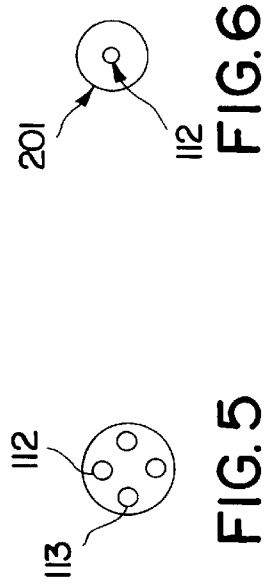
FIG. 3
FIG. 4
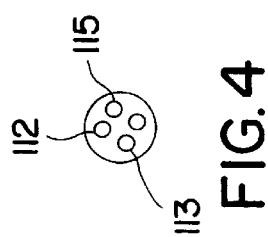
FIG. 5
FIG. 6

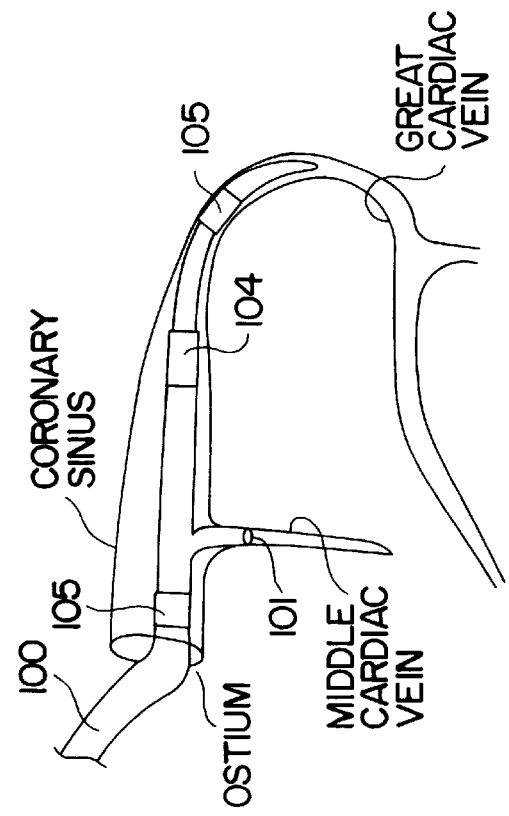
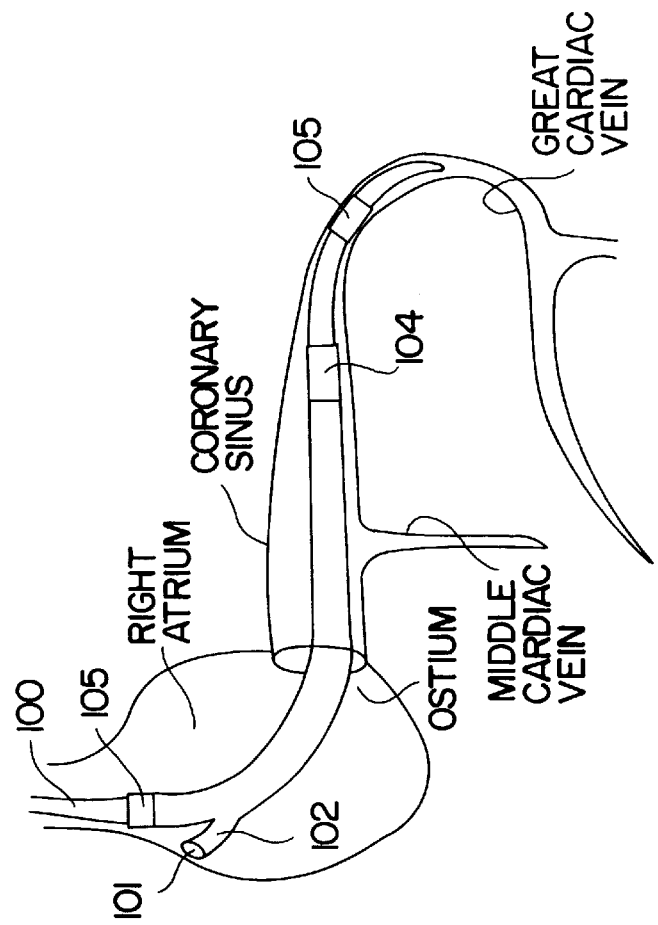
FIG. 7A
FIG. 7B

MEDICAL ELECTRICAL RIGHT ATRIUM AND CORONARY SINUS LEAD

FIELD OF THE INVENTION

This invention relates to the field of body implantable medical device systems, and in particular to a body implantable medical device system which includes a medical electrical lead particularly designed for providing multi-chamber electrical stimulation or sensing.

BACKGROUND OF THE INVENTION

Modern electrical therapeutic and diagnostic devices for the heart, such as pacemakers, cardiovertors, and defibrillators, for example, require a reliable electrical connection between the device and a region of the heart. Typically, a medical electrical "lead" is used for the desired electrical connection.

One type of commonly used implantable lead is a transvenous lead. Transvenous leads are positioned through the venous system to attach or electrically connect at their distal end to the heart. At their proximal end, they are connected to typically an implantable pulse generator. Such leads normally took the form of a long, generally straight, flexible, insulated conductor. Among the many advantages of a transvenous lead is that it permits an electrical contact with the heart without physically exposing the heart itself, i.e., major thoracic surgery is not required.

The specific design of a transvenous lead used is often varied depending upon the region of the heart to which it is to be connected. For example, U.S. Pat. No. 4,402,330 of Lindemans discloses a body implantable lead in which the lead body has a J-curve and the distal electrode has a permanent bend. In such a manner, the lead is configured to electrically connect to the right atrium.

While such a lead has been found acceptable for electrically connecting and thus pacing the right atrium, the need exists for a transvenous medical electrical lead which may provide an electrical connection to the left atrium. Of course the left atrium cannot, at present, be transvenously accessed with a lead for chronic implantation due to the direction of blood flow and the present limitations of materials. To be precise, blood flows through the right side of the heart (atrium and ventricle), through the lungs, through the left side of the heart (atrium and ventricle) and then through the rest of the body, including the brain, before returning again to the right side of the heart. Implanted objects, however, often cause minor blood clots and thrombus to form in the blood. These may, on occasion, dislodge and be released into the bloodstream. Because the blood circulates directly from the left atrium and ventricle to the brain, any clots, however minor, could have serious consequences if they were to reach the brain, e.g. a stroke. In contrast, any clots released from an object implanted in the right side of the heart would simply travel to the lungs, where they would lodge without any serious risk. Thus at present, chronic transvenous leads may not be safely implanted within the left side of the heart.

In spite of the difficulties, there remains a great need to be able to electrically stimulate or sense or both the left side of the heart. The most obvious reason is the left side of the heart accounts for the majority of the heart's hemodynamic output. For example, the left ventricle has a greater wall thickness (10–20 mm as compared to 1–5 mm) than the right side. This, of course, is reasonable given that the left side of the heart must pump blood throughout the body while the right side only pumps blood through the lungs.

Because the left side is relatively more important for hemodynamic output, not surprisingly various pathologies may be better treated through stimulation on the left side of the heart. For example, in patients with dilated cardiomyopathy, electrical stimulation of both the right side and the left side of the heart has been shown to be of major importance to improve the patient's well-being and manage heart failure. See, for example, Cazeau et al., "Four Chamber Pacing in Dilated Cardiomyopathy," PACE, Nov. 1994, pgs. 1974–79. See also Brecker and Fontainem, St. et al., "Effects Of Dual Chamber Pacing With Short Atrioventricular Delay In Dilated Cardiomyopathy," Lancet Nov. 1992 Vol. 340 p1308–1312; Xiao HB et al., "Effect Of Left Bundle Branch Block On Diastolic Function In Dilated Cardiomyopathy," Br. Heart J 1991, 66(6) p 443–447; and Fontaine G et al, "Electrophysiology Of Pseudofunction," CI.Meere (ed.) Cardiac pacing, state of the art 1979, Pacesymp, 1979 Montreal.

Many times the left side is to be electrically stimulated or sensed, the right atrium is also to be electrically stimulated or sensed. At present such multi-chamber pacing is accomplished using two separate leads, one for the right atrium and one for the left. Such a multi-lead system for left and right side therapy, however, has several drawbacks.

First, the two separate lead bodies may rub, over time leading to a breach in the insulative sheath and lead failure. Second, because two leads are required the cost of the entire system is correspondingly higher. In addition, the implant time, because two leads must be implanted, is also greater than if one lead could be used. Moreover, the two leads have a greater surface area exposed to the blood as compared to a single lead system. Although current surfaces of leads are highly successful, it is nonetheless a goal of all lead designs to minimize the surface area of the lead exposed to the blood to thereby decrease the possibility of any adverse blood-device reactions, e.g. thrombus.

Besides the problems inherent in a multi-lead system, there are still further difficulties with implanting and fixing a lead within the coronary sinus. Unlike a heart chamber where the fibrotic tissue response is used to assist lead fixation, no such fibrotic response can be expected to occur within the coronary sinus. As such no fibrotic tissue response is available to assist in lead fixation. Moreover, blood flow through the coronary sinus tends to sweep out any leads implanted therein. Finally the coronary sinus also presents the unique challenge that any lead must be fixed without the assistance of trabeculae, those structures in the right atrium and ventricle used for maintaining lead position.

It is thus an object of the present invention to provide a medical electrical lead which may be used to electrically access both the right atrium as well as either or both of the left chambers of the heart.

A still further object of the present invention is to provide such a medical electrical lead which may be used to electrically access both the right atrium as well as either or both of the left chambers of the heart and may be reliably fixed within the coronary sinus.

SUMMARY OF THE INVENTION

These and other objects are accomplished through the present invention. In one embodiment, the present invention comprises a transvenous lead specifically designed for multi-chamber electrical stimulation or sensing. In a first embodiment the lead features one or more electrodes for communication with the right atrium as well as one or more electrodes for communication with either or both of the left chambers of the heart. The lead further features structures to simultaneously bring the first electrode into contact with a first chamber, such as the right atrial wall and the second electrode into contact with a particular portion of the coronary sinus wall, to electrically access the left atrium or ventricle. In the preferred embodiment the lead body has varying flex or stiffness characteristics along its length between each of the electrodes. The relation of the varying flex or stiffness characteristics along the lead body length as well as the various linear placements of the electrodes along the lead body length function to simultaneously bring the first electrode into contact with a first desired portion of the heart, such as the right atrial wall, and the second electrode into contact with a second desired portion of the heart, such as a portion of the coronary sinus wall. In a first embodiment the distal section of lead body extends for a distance between the distal most tip of lead body and an electrode for a distance of between approximately 1–5, with 3 cm preferred and this section has the greatest flexibility of any of the remaining linear section of lead body. A middle lead body portion of this embodiment extends from the first electrode to a second electrode for a distance of between approximately 0.5–4, with 1.5 cm preferred, and this section has the greatest flexibility of any of the other remaining linear section of lead body (i.e. it is less flexible as compared to distal section). Next a further section of the lead features a tine having an electrode, this section is positioned from second electrode a distance of between approximately 2–8 cm, with 5 cm preferred. This section has the least flexibility of any of the sections of lead body. This diminished flexibility functions to wedge or cause the various electrodes to be brought into simultaneous contact with the right atrial wall and the coronary sinus wall.

BRIEF DESCRIPTION OF THE FIGS.

FIG. 2 is a side of the lead shown in FIG. 1.

FIG. 3 is a cross-sectional view of the lead shown in FIG. 2 taken along the lines 3—3.

FIG. 4 is a cross-sectional view of the lead shown in FIG. 2 taken along the lines 4—4.

FIG. 5 is a cross-sectional view of the lead shown in FIG. 2 taken along the lines 5—5.

FIG. 6 is a cross-sectional view of the lead shown in FIG. 2 taken along the lines 6—6.

FIGS. 7A and 7B show the various areas within the heart where a lead constructed with different dimensions may be implanted.

It should be understood the drawings are not necessarily to scale.

DETAILED DESCRIPTION OF THE INVENTION

The present invention concerns a single lead which may be provided to stimulate or sense or both the right atrium as well as a chamber or chambers of the left side of the heart through the coronary sinus. As is well known, there has to date been a great difficulty in reliably implanting leads within the coronary sinus. For example, a typical coronary sinus is 10 millimeters at its largest diameter (near the outflow to the right atrium) and narrows until it has a diameter of between approximately 2–3 millimeters and merges to the great cardiac vein. Thus any leads having larger sizes could be expected to detrimentally diminish if not completely occlude the flow of blood through the coronary sinus. The fixation of a lead within the coronary sinus is further complicated by the fact that, unlike a heart chamber where the fibrotic tissue response is used to assist lead fixation, no such fibrotic response can be expected in the vein. As such no fibrotic tissue response is available to assist in lead fixation. Thus the present invention includes a lead specifically tailored to this environment so that this single lead may be stimulate or sense or both the right atrium as well as a chamber or chambers of the left side of the heart through the coronary sinus.

Figure 1:
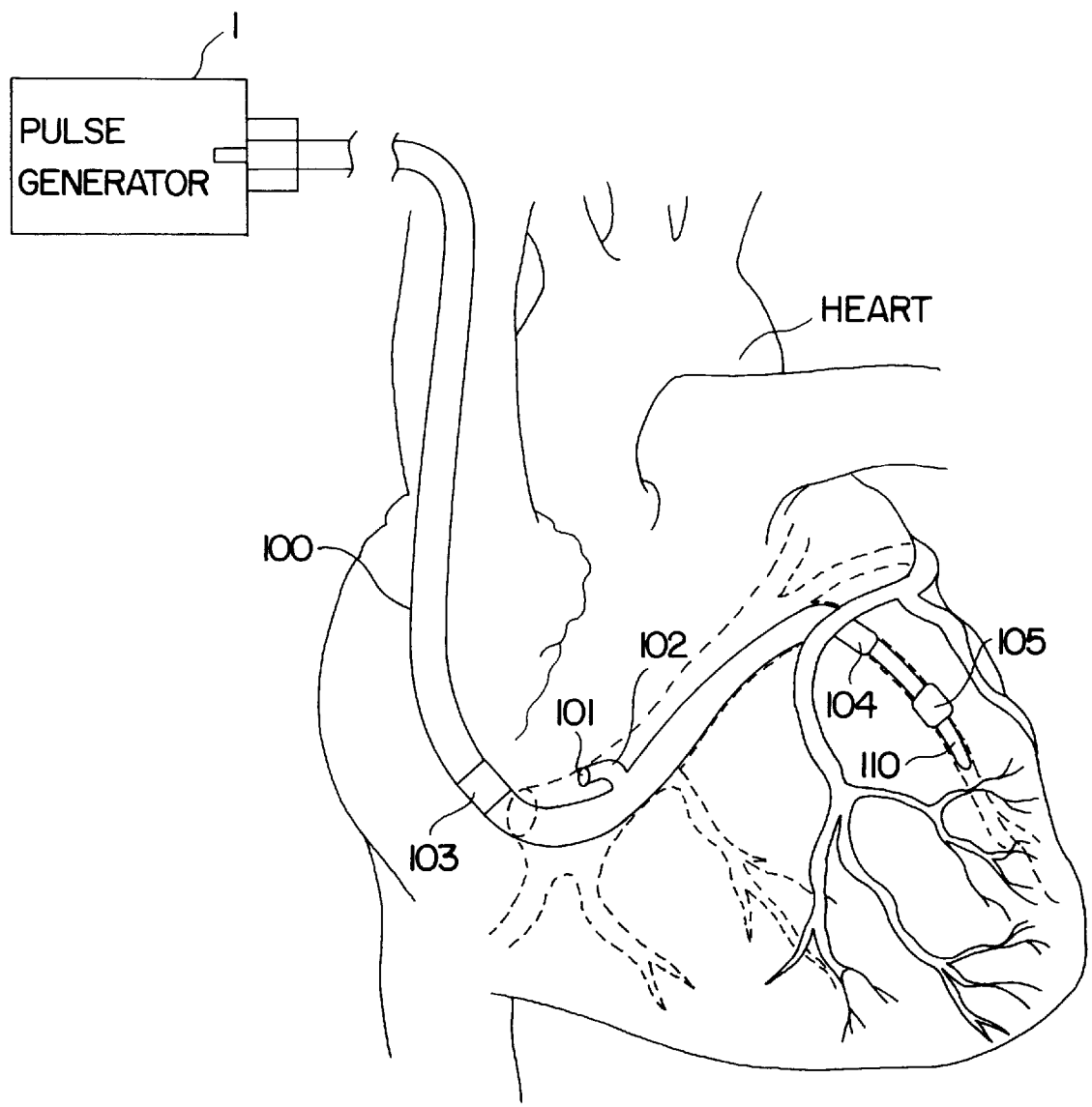
FIG. 1 is a perspective view of a lead according to the present invention shown implanted in a heart.

FIG. 1 is a first embodiment of the present invention featuring such a lead disposed within a heart. As seen in this embodiment pulse generator 1 is coupled to a lead 100. Pulse generator may be any model capable of sensing and stimulating three or more chambers of the heart. Lead 100 features an electrode 101 eccentrically placed along the lead by having it placed at the distal end of a tine 102. As further seen, in this embodiment lead may feature one or more ring electrodes disposed along the lead body. In the illustrated embodiment three ring electrodes 103, 104 and 105 are shown. This embodiment further features a molded nose 110 which extends beyond the distal most electrode so as to improve maneuverability within the tortuous cardiac veins. Finally, the present invention further features a lead body having varying flex or stiffness characteristics along its length between each of the electrode structures. As more fully described below, the relation of the varying flex or stiffness characteristics along the lead body length as well as the various linear placements of the electrodes along the lead body length permit the lead of the present invention to reliably pace or sense or both the right atrium, the left atrium, the left ventricle or any combination thereof. In particular, these parameters effectively cause the electrodes to be wedged between the right atrial wall and the coronary sinus. Such wedging ensures excellent contact is maintained between the electrodes and the heart while also ensuring the lead remains in the positioned into which it is placed.

FIG. 2 is a side view of lead 100 shown in FIG. 1 and best showing the disposition of blunted tapered nose 110 relative to electrodes. As seen lead 100 is constructed of a multi lumen lead body 110, preferably constructed of a biocompatible polymer, such as silicone. As also seen in this view electrode 105 is disposed so that it has a larger diameter that the lead body in that vicinity. In the preferred embodiment electrode 105 has a diameter between approximately 1.5–3.5 mm with 2.5 mm preferred, selected so as to be greater by an amount of at least 1 mm greater than the lead body and preferably approximately 2 mm greater than the remainder of the lead body. Such a larger diameter is important because the electrode 105 functions as a cathode, and thus must achieve solid contact with the wall to have acceptable thresholds and pacing impedances. This view further illustrates the relation of the sections of the lead body which have varying flex or stiffness characteristics as compared to the other portions of the lead body as well as the various linear placements of the electrodes along the lead body length.

As seen in FIG. 2, distal section of lead body 200 extends from the distal most tip 911 of lead body and electrode 105 for a distance of between approximately 1–5 cm, with 3 cm preferred and this section has the greatest flexibility of any of the remaining linear sections of lead body. As seen this flexibility is provided through the combination of the centrally positioned coiled conductor, the thickness of the insulative sheath as well as the tapering of the sheath in this area. Of course, flexibility may be provided and adjusted in many other ways well known in the art, including the use of differing materials as well as the design of the various components, e.g. alternating the geometry of the conductor or the coil or the insulation thickness or even the addition or omission of a separate stiffening member. The exact means by which such a result is accomplished is not critical to the operation of the present invention.

Next middle lead body portion 201 extends from electrode 105 to electrode 104 for a distance from electrode 105 and electrode 104 between approximately 0.6–2.8 cm, with 1.5 cm preferred. This section has the greatest flexibility of any of the other remaining linear section of lead body (i.e. it is less flexible as compared to distal section 200). Like above, the flexibility of the lead in this section is tailored through the thickness of the insulative sheath as the coiled conductor. In particular, this section preferably features a length of insulative sheath having a greater thickness and thus stiffness as compared to that of section 200. Of course, like the section described above, the flexibility may also be provided and adjusted in many other ways well known in the art, including the use of differing materials as well as the design of the various components.

Next tine section 202 includes tine 102. Tine 102 is located at a distance from electrode 104 of between approximately 2–8 cm, with 5 cm preferred. Tine section 202 further includes a span of lead body from the base of tine 102 to electrode 103 which runs for a distance of between approximately 0.1–2 cm, with 0.5 cm preferred. Tine 102 is itself between approximately 1–15 mm with 5 mm preferred. Tine section 202 has the least flexibility of any of the sections of lead body. In particular, this section preferably features a length of insulative sheath as well as a pair of side by side coiled conductors which, in combination, are less flexible as compared to all other sections of the lead body. Of course, like the section described above, the flexibility may also be provided and adjusted in many other ways well known in the art, including the use of differing materials as well as the design of the various components, including the design of the conductors, as well as the relative positions of the conductors within the lead body.

Finally proximal section 203 extends from electrode 103 to connector pin assembly for a distance of between approximately 45–110 cm, with 65 cm preferred. Section 203 has a stiffness equal to or less than section 202. As above the flexibility may also be provided and adjusted in many other ways well known in the art, including the use of differing materials as well as the design of the various components.

It must be understood that the particular dimensions selected for any section or component of the lead are crucial and essential to the effective operation of the present invention.

FIG. 3 is a cross sectional view of the lead shown in FIG. 2 taken across line 3—3. In this section, proximal to electrode 103, lead body carries four conductors, 112, 113, 114, 115 each housed within a corresponding lumen within lead body. Conductors are preferably constructed of a biocompatible conductor, such as MP35N. Conductor 114 couples to electrode 103, preferably functions as the anode relative to electrode 101 and is a whole ring of a polished platinum iridium alloy having a surface area of 36 sq. mm.

FIG. 4 is a cross sectional view of the lead shown in FIG. 2 taken across line 4—4. In this section only three of the four lumens house conductors 112, 113 and 115. As best seen in FIG. 4, conductor 115 couples to electrode 101 positioned at tip of tine 102. Electrode 101 may be of any suitable construction and preferably is constructed using a platinized porous material such as a platinized spherical sintered platinum powder as is well known in the art and has a surface area of between approximately 1.2–8.0 sq. mm. with 5.8 sq. mm. preferred.

FIG. 5 is a cross sectional view of the lead shown in FIG. 2 taken across line 5—5. In this section only two of the three lumens house conductors 112 and 113.

FIG. 6 is a cross sectional view of the lead shown in FIG. 2 taken across line 6—6. In this section only, because conductor 114 coupled to electrode 103 and conductor 115 coupled to electrode 101 and conductor 113 coupled to electrode 104 only a single conductor 112 remains and thus along this section lead body is a single lumen construction. Referring back to FIG. 2, as seen, this single lumen, however, extends for a distance distally beyond electrode 105 and into a tapered nose 110 of the lead body.

FIGS. 7A and 7B show the various areas within the heart where a lead constructed with different dimensions may be implanted. As seen, the present invention is compatible for use with multi-chamber stimulation or sensing. In FIG. 7A the distance between electrode 105 (and of course tine 102) and electrode 104 is at the larger size of its given range, thus permitting left atrial and right atrial contact to be made. Moreover, due to the stiffness of the lead body between these electrodes, as well as the tine, the electrical contact with the tissues is ensured. In turn, this also ensures good electrical performance of the entire system. In FIG. 7B the distance between electrode 105 (and of course tine 102) and electrode 104 is at the smaller size of its given range. In addition the entire lead is implanted further within the coronary sinus and oriented so the tine is introduced within the middle cardiac vein. Ultimately this permits electrical stimulation and sensing to be accomplished for the left atrium and the left ventricle.

Figure 8:
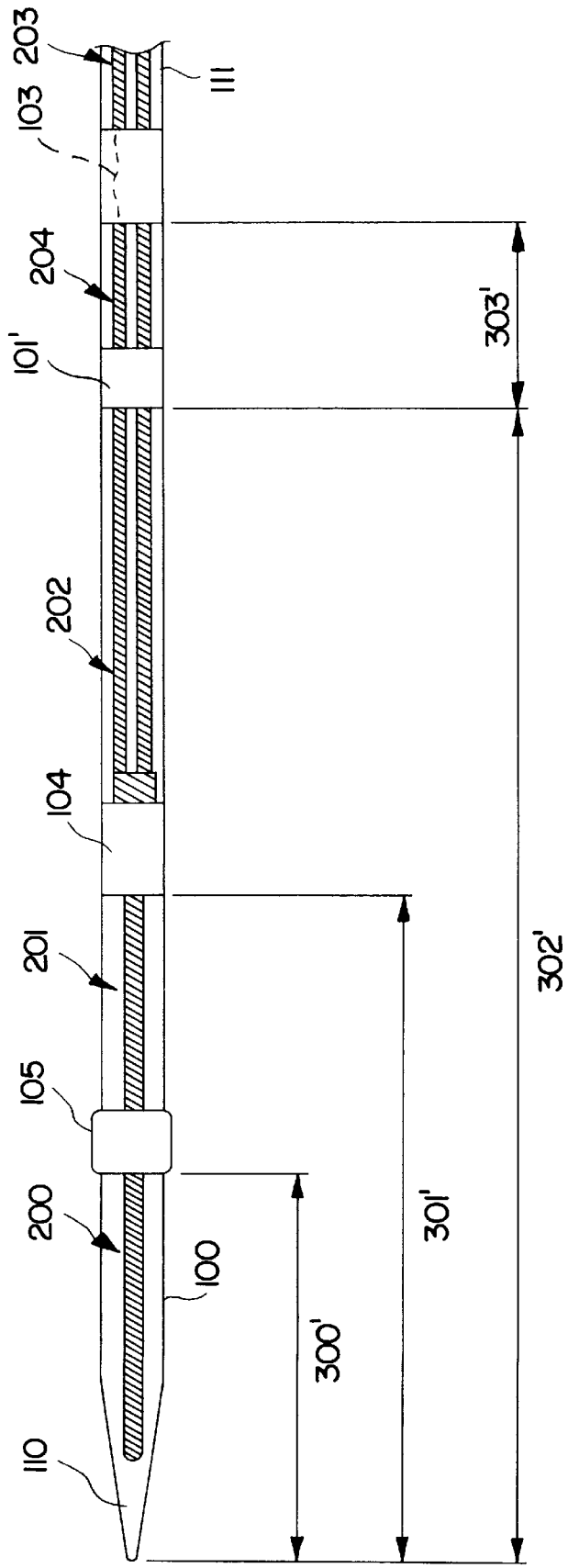
FIG. 8 depicts an alternative embodiment of the present invention.

FIG. 8 depicts an alternative embodiment of the present invention. In particular this embodiment is substantially the same as that shown in FIGS. 1–6 but for the provision of a ring electrode 101' as compared to the electrode 101 on tine in the previous embodiment. In this embodiment, distal section of lead body 200 extends for a distance 300' between the distal most tip of lead body and electrode 105 for a distance of between approximately 1–5 cm, with 3 cm preferred and this section has the greatest flexibility of any of the remaining linear sections of lead body.

Next electrode 104 is positioned a distance 301' from the distal most tip of lead body between approximately 5.0–6.9 cm, with 5.4 cm preferred. Middle lead body portion 201, defined between electrode 105 and electrode 104 has less flexibility as compared to the distal section 200.

Next electrode 101' is positioned a distance 302' from the distal most tip of lead body between approximately 11.0–15.0 cm, with 13.0 cm preferred. Lead body portion 202, defined between electrode 104 and electrode 101' has less flexibility as compared to the distal section 200 and preferably the same as middle lead body portion 201.

Next electrode 103 is positioned a distance 303' from electrode 101' between approximately 0.1–1.5 cm, with 0.5 cm preferred. Lead body portion 204, defined between electrode 101' and electrode 103 has less flexibility as compared to the distal section 200 and preferably the same as middle lead body portion 201 and lead body portion 202.

Finally, the total lead body length, from the distal most tip of lead body to the connector pin (not seen in this view) is between approximately 45–110 cm with 65 cm preferred.

In this embodiment, like that already discussed above, the Of course, like the section described above, the varying flexibility characteristics along the lead body may be provided and adjusted in many of the numerous ways well known in the art, including the use of differing materials as well as the design of the various components, including the design of the conductors, as well as the relative positions of the conductors within the lead body. Like that already discussed above the particular mechanism selected is not critical.

Figure 9:
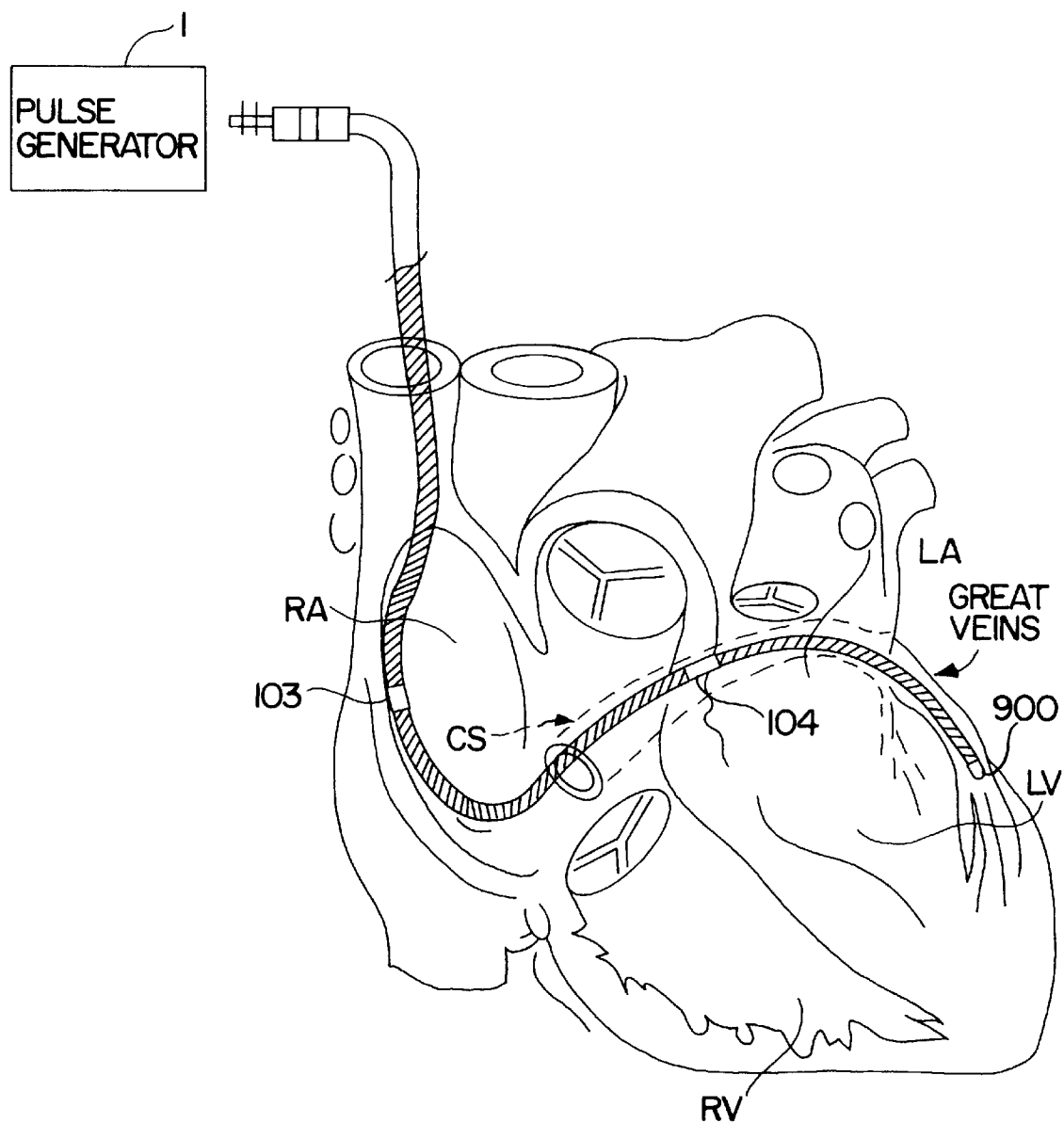
FIG. 9 depicts an alternative embodiment of the present invention shown implanted in a heart.

FIG. 9 depicts an alternative embodiment of the present invention shown implanted in a heart. In particular this embodiment is designed with only three electrodes and positioned to make electrical contact with the left ventricle, the left atrium and the right atrial wall. Thus as seen the lead body is designed to position one or more electrodes directly against the right atrial wall.

Figure 10:
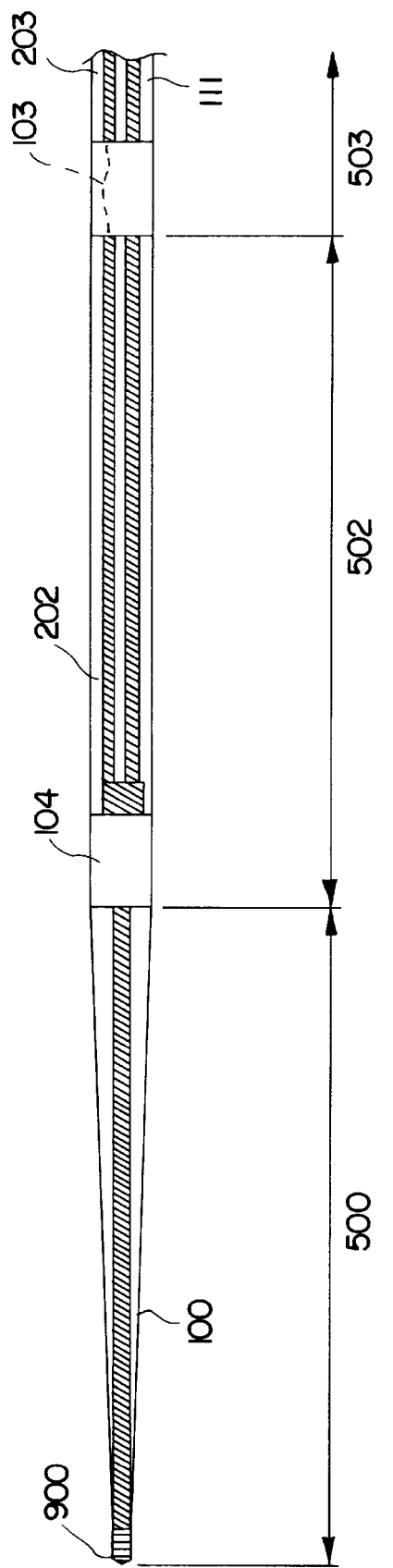
FIG. 10 is a side view of the lead shown in FIG. 9.

FIG. 10 is a side of the lead shown in FIG. 9. As seen electrode 900 is positioned at the distal most end of the lead body. Electrode 104 is positioned away from the distal most end of the lead body a distance 500 between approximately 4–12 cm with 8.6 cm preferred. Lead body 100 has a taper so as to increase the flexibility of lead body as well as decrease the diameter of lead body as a function of proximity to the distal most end. As also seen, this portion of lead body features a single coiled conductor, as is well known in the art.

Next, electrode 103 is positioned away from electrode 104 a distance 502 between approximately 5–9 cm with 7.5 cm preferred. The lead body along this portion 202 is designed to be the most stiff of any other portion of the lead. Stiffness may be accomplished in any of the known, acceptable ways, including varying the conductor configuration, as well as increasing or decreasing insulation thickness. As also seen, this portion of lead body features a pair of side by side coiled conductors, as is well known in the art.

Finally, the total lead body length, from the distal most tip of lead body to the connector pin (not seen in this view) is between approximately 45–110 cm with 65 cm preferred.

Each of the electrodes may further be constructed having a cavity into which is disposed a monolithic controlled release device therein to elute or dispense a drug, such as the sodium salt of dexamethasone, from the electrode into the surrounding tissues, as is well known in the pacing art. In an alternative, the electrodes may be treated with a very slightly soluble in water steroid, such as beclomethasone dipropionate anhydrous. Preferably the steroid is applied to the surface of the electrode which contacts tissue when implanted. Further details of such a coating process may be found in the copending U.S. patent application of Williams "Medical Electrical Lead" Ser. No. 08/604,591, incorporated herein by reference.

It must be understood that the particular dimensions selected are crucial and essential to the effective operation of the present invention.

It is to be understood that the present invention is not limited to use only in pacing leads, and may be employed in the construction of may of various type of therapeutic and diagnostic devices, including defibrillation leads, intended to be disposed within the coronary sinus. In fact, for the purposes of this specification and claims, the term "lead" is used herein in its broadest sense and includes any stimulation lead or sensing lead, a combination thereof or any other elongated member, such as a catheter, which may usefully be introduced into a body. For purposes of illustration only, however, the present invention has been described in the context of transvenous pacing lead. Moreover, the present invention may be used in any of the various venous and arterial pathways along the heart or anywhere else within the body, thus the term "coronary sinus" is also used herein in its broadest sense and includes, without limitation, the great cardiac vein or any other cardiac vessel.

Although a specific embodiment of the invention has been disclosed, this is done for purposes of illustration and is not intended to be limiting with regard to the scope of the invention. It is contemplated various substitutions, alterations and/or modifications may be made to the disclosed embodiment without departing from the spirit and scope of the invention. Such modifications may include substituting elements or components which perform substantially the same function in substantially the same way to achieve substantially the same result for those described herein.

What is claimed is:

1. A medical electrical lead comprising means for electrically coupling to a pulse generator a lead body coupled to the means for electrically coupling, the lead body having a first distal end, a second proximal end, the lead body comprising a conductor insulated by an insulative sheath, a first electrode positioned along the lead body;

a second electrode positioned along the lead body and proximal to the first electrode; and means for simultaneously bringing the first electrode into contact with a coronary sinus wall and the second electrode into contact with a right atrial wall.

2. A medical electrical lead according to claim 1 wherein the means for simultaneously bringing the first electrode into contact with the coronary sinus and the second electrode into contact with the right atrial wall comprises a first and second section of the lead body, the first section extending between the distal end of the lead and the first electrode for a distance of between approximately 1–5 cm and the second section extending between the first electrode and the second electrode for a distance of between approximately 2–8 cm.

3. A medical electrical lead according to claim 2 wherein the second section is less flexible as compared to the first section.

4. A medical electrical lead according to claim 2 wherein the lead body further having a tine positioned proximal to the second electrode at distance of between approximately 0.1–2 cm.

5. A medical electrical lead according to claim 4 wherein the tine extending away from lead body a distance of between approximately 1 mm–15 mm, the tine having a tip, a third electrode positioned on the tip.

6. A medical electrical lead according to claim 1 wherein the first electrode has a first diameter and the lead body has a lead body diameter, the first electrode diameter greater than the lead body diameter.

7. A medical electrical lead according to claim 1 wherein the first electrode is a whole ring electrode and has a first diameter and the lead body has a lead body diameter, the first electrode diameter greater than the lead body diameter by an amount of at least 1 mm greater than the lead body.

8. A medical electrical lead according to claim 7 wherein the first electrode diameter is between approximately 1.5–3.5 mm.

9. A medical electrical lead according to claim 1 wherein the first electrode is positioned between approximately 1–5 cm. from the first distal end.

10. A medical electrical lead according to claim 1 wherein the first distal end comprises a tapered blunt nosed portion constructed of a pliable polymer.

11. A medical electrical lead comprising
means for electrically coupling to a pulse generator;
a lead body coupled to the means for electrically coupling, the lead body having a first distal end, a second proximal end, the lead body comprising a conductor insulated by an insulative sheath, the first distal end comprises a tapered blunt nosed portion, a lumen in the lead body communicating from the second proximal end to a lumen end point, the lumen end point proximal to the first distal end;
a first electrode positioned along the lead body at a point proximal to the lumen end point, the first electrode is a whole ring electrode and has a first diameter and the lead body has a lead body diameter, the first electrode diameter greater than the lead body diameter by an amount of at least 1 mm greater than the lead body diameter;
a second electrode positioned along the lead body and proximal to the first electrode; and
means for simultaneously bringing the first electrode into contact with a coronary sinus wall and the second electrode into contact with a right atrial wall.

12. A medical electrical lead according to claim 11 wherein the means for simultaneously bringing the first electrode into contact with the coronary sinus and the second electrode into contact with the right atrial wall comprises a first and second section of the lead body, the first section extending between the distal end of the lead and the first electrode for a distance of between approximately 1–5 cm and the second section extending between the first electrode and the second electrode for a distance of between approximately 2–8 cm.

13. A medical electrical lead according to claim 12 wherein the second section is less flexible as compared to the first section.

14. A medical electrical lead according to claim 12 wherein the lead body further having a tine positioned proximal to the second electrode at distance of between approximately 0.1–2 cm.

15. A medical electrical lead according to claim 14 wherein the tine extending away from lead body a distance of between approximately 1 mm–15 mm, the tine having a tip, a third electrode positioned on the tip.

16. A medical electrical lead according to claim 11 wherein the first electrode has a first diameter and the lead body has a lead body diameter, the first electrode diameter greater than the lead body diameter.

17. A medical electrical lead according to claim 11 wherein the first electrode is a whole ring electrode and has a first diameter and the lead body has a lead body diameter, the first electrode diameter greater than the lead body diameter by an amount of at least 1 mm greater than the lead body.

18. A medical electrical lead according to claim 17 wherein the first electrode diameter is between approximately 1.5–3.5 mm.

19. A medical electrical lead according to claim 11 wherein the first electrode is positioned between approximately 1–5 cm. from the first distal end.

20. A medical electrical lead according to claim 11 wherein the second electrode is positioned between approximately 5–15 cm. from the first distal end.

* * * * *